US006482782B1

(12) United States Patent
Kim

(10) Patent No.: US 6,482,782 B1
(45) Date of Patent: Nov. 19, 2002

(54) SOAP BAR HAVING A SOAP BASE CONTAINING AMINO ACID DERIVATIVE AND A COATED MICACEOUS POWDER

(76) Inventor: Sung-O Kim, 326-404, Jugong Apt., 20-9, Banpo-dong, Seocho-gu, Seoul (KR)

( * ) Notice: Subject to any disclaimer, the term of this patent is extended or adjusted under 35 U.S.C. 154(b) by 0 days.

(21) Appl. No.: 09/709,286

(22) Filed: Nov. 13, 2000

(51) Int. Cl.[7] .................................................. A61K 7/50

(52) U.S. Cl. ....................... 510/141; 510/151; 510/155; 510/153; 510/447

(58) Field of Search ................................ 510/141, 151, 510/155, 153, 447

(56) References Cited

U.S. PATENT DOCUMENTS 5,296,159 A * 3/1994 Wilson et al. .............. 252/117
5,703,026 A * 12/1997 Setser et al. ................ 510/152

FOREIGN PATENT DOCUMENTS

KR 1988-1858 9/1988

* cited by examiner

*Primary Examiner*—Necholus Ogden
(74) *Attorney, Agent, or Firm*—Bacon & Thomas

(57) ABSTRACT

The present invention relates to an weak acidic soap bar which can represent a pearly appearance, a noble color quality and a high luster which is prepared by mixing a soap base composition comprising amino acid derivatives having a melting point of below 100° C. and a coated micaceous powder, and molding the mixture. The soap bar according to the present invention is excellent in aspects of soap quality, color sense and appearance by mixing specific amino acid derivatives base and a coated micaceous powder, dissolving, and molding the mixture.

7 Claims, No Drawings

SOAP BAR HAVING A SOAP BASE CONTAINING AMINO ACID DERIVATIVE AND A COATED MICACEOUS POWDER

BACKGROUND OF THE INVENTION

1. Field of the Invention

The present invention relates to an weak acidic soap bar having a pearlescent pattern, a noble color sense and a high luster which is prepared by mixing a soap base composition comprising amino acid derivatives having a melting point of below 100° C. with a coated micaceous powder, and then molding the mixture.

2. Description of the Prior Art

Soap bars are generally prepared by directly gelling raw material oils and fats of sodium salts of higher fatty acids or the mixture thereof with sodium hydroxide in aqueous phase and then separating the sodium salts(soap base) and glycerine by desalting or by a direct reaction of fatty acids and sodium salts. Such soap bars have a high melting point and are thus prepared by the steps of mixing raw materials, extruding and molding.

Meantime, a striation soap bar is described in Korean Patent Publication No 88-1858. This soap bar is prepared by a process in which each of the soap base materials are striation materials is extruded through two sets of pressers vertically connected to a connection head However, the soap bars thus prepared have a drawback upon actual use that since the different soap bases are integrated through the pressers, the soap bar is easily dried to result in the separation of each component in use and, therefore, the resulting soap bar cannot be effectively used.

In addition, the conventional cosmetic soap bar having a pearly appearance is prepared by mixing a soap base with glycerine, water and a powder in a specific ratio. However, since this prior art process employs the steps of simple mixing of the raw materials and extrusion of the mixture to give the soap bar with the appearance of a wood grain or a pearly pattern which results in dissolution of the soap bar and dispersion of the powder due to it's high melting temperature of above 200° C., this soap bar cannot afford a naturally formed luster and high quality of a soap bar. Therefore, the prior art process, which comprises simple mixing of the conventional soap bar base composition with a powder, has a drawback in providing various lusters and soap bar quality.

SUMMARY OF THE INVENTION

The present inventor has been extensively studied in order to solve the above mentioned problem and, as a result, found that a soap bar base composition prepared by employing amino acid derivatives as a base and mixing the base with a prescribed amount of saccharide such as sugar, di-glycerine, 1,3-butylene glycol, and polyols, and a minor amount of a soap powder and surfactants and then dissolving the mixture into water-lower alcohols under heating can be dissolved at a temperature of below 100° C. and, based on this finding, has succeeded in preparing a soap bar having a pearlescent pattern which shows a naturally formed luster and a high color quality such as a pearl shampoo by mixing the base composition and a coated micaceous powder to effect maximum dispersion and molding and, has completed the present invention.

Therefore, an object of the present invention is to provide a soap bar having a naturally formed pearlescent pattern and a high luster and a noble color quality by dispersing a coated micaceous powder into the soap base composition comprising amino acid derivatives of which melting point is below 100° C.

Another object of the present invention is to provide a soap bar having a unique pearlescent pattern, a noble color quality and a high luster prepared by mixing the soap base composition comprising amino acid derivatives with a coated micaceous powder, dissolving and molding the mixture.

DETAILED DESCRIPTION OF THE INVENTION

The present invention provides a soap bar having a pearlescent pattern, a noble color quality and a high luster prepared from the soap base composition comprising amino acid derivatives of which melting point is below 100° C. and a coated micaceous powder.

The soap bar according to the present invention is prepared by mixing the soap base composition comprising amino acid derivatives with a coated micaceous powder, dissolving and molding the mixture.

The term, "the soap base composition comprising amino acid derivatives" used throughout the specification has no limitation as long as it has a melting point of below 100° C. and encompasses any conventional base material for the soap bar. The amino acid derivatives which can be used in this context include, for example, TEA-cocoyl glutamate, TEA-lauroyl glutamate, TEA-stearoyl glutamate, or the mixture thereof, As the additional components for the soap base, one or two or more of components selected from the group consisting of ethanol, 1,3-butyleneglycol, sodium palmitate, sodium laurate, di-glycerine, sorbitol, $C_8$–$C_{14}$alkylpolyglycoside(for example, cocoyl glycoside), sodium hydroxide, ethylenediaminetetraacetic acid disodium, tocopheryl acetate, urea, fragrance and water may be added to the soap base composition. In addition, sodium lauryl sulfate, polyoxyethylene sodium laurylether sulfate, dibutylhydroxytoluene, calcium hydroxide, etc., in an appropriate amount may be mixed into the soap base composition.

As a consequence of the test for various mixing ratio for the above base, it was confirmed that the preferable composition comprises 18.90~22.50% of TEA-cocoyl glutamate, 17.20~25.80% of TEA-lauroyl glutamate, 26.60~30.50%, of TEA-stearoyl glutamate, 2.00~4.50% of ethanol, 1.50~3.50% of 1,3-butyleneglycol, 1.20~3.50% of sodium palmitate, 1.00~2.60% of sodium laurate, 1.50~3.50% of di-glycerine, 1.00~3.40% of sorbitol, 0.50~2.50% of $C_8$–$C_{14}$alkylpolyglycoside, 0.12~2.80% of sodium hydroxide, 0.05~0.15% of ethylenediaminetetraacetic acid disodium, 0.05~0.15% of tocopheryl acetate, 0.05~0.15% of urea based on the weight, fragrance and water.

It is preferable that said base composition is contained in an amount of about 90~99.99% based on the weight of the raw materials for the soap bar, especially the range of about 95~99.99% being more preferable.

The term, "a coated micaceous powder" as used in this specification is meant by the powder in which mica is coated with, for example, titanium dioxide, and/or other component (s). More specifically, mica can be coated with titanium dioxide, and/or one or more components selected from the group consisting of tin oxide, iron oxides such as black iron oxide(ferrous-ferric oxide, $Fe_3O_4$) and red iron oxide(ferric oxide, $Fe_2O_3$), iron blue(ferric ferrocyanide), carmine, chromium oxides such as chromium oxide greens. More specifically, mica is coated, for example, with titanium dioxide, with titanium dioxide, with titanium dioxide and tin oxide, with titanium dioxide and black iron blue, with titanium dioxide and carmine, with titanium dioxide and chromium oxide, with black iron oxide, or with red iron oxide. In addition to these pigments, any component can be used for the coated micaceous powder provided that they can impart a pearlescent pattern, a high luster and a noble color quality to the soap bar. For example, the known pigment products for cosmetic or soap bars which are commercially available from the Merarl Corporation or the Merck & Co., Inc. can also be used. This additive component can be a combination of two or more components. The mixing ratio of the components within the powder has no specific limitation, however, it is preferable to use mica in an amount of below 80%, titanium dioxide in an amount of below 60%, tine oxide in an amount of below 5%, black iron oxide in an amount of below 60%, red iron oxide in an amount of below 60%, iron blue in an amount of 10%, carmine in an amount of 5%, and chromium oxides in an amount of below 20% based on the weight of the powder. It will be, however, appreciated that the above amounts are illustrated as an example only, and any combination of the ingredients in any mixing ratio is within those skilled in the art. Therefore, any combination of the ingredients in the powder is within the scope of the present invention. It is preferable to use the powder in an amount of about 0.01% to 10% based on the weight of soap bar. If the amount of the powder is below 0.01% by weight, the pearly appearance and luster of the soap bar are faded or disappear. If the amount is above 10% by weight, the soap bar will have a high luster, but is difficult for representing a variety of colour quality of the soap bar. Further, the addition of the coated micaceous powder has an additional advantage that the bubbling power and the hardness of the soap bar are increased.

The coated micaceous powder can be pre-formed according to the conventional process prior to the mixing with the soap base composition. The powder which can be used in the present invention has a particle size of about 5~500 $\mu$m and various particle size distribution of the coated powder can be used in the preparation of the soap bar according to the invention. Particularly, the coated powder having a particle size of below 150 $\mu$m provides excellence in aspects of the pearly luster and the colour quality of the soap bar. The most preferable particle size of the coated powder is in the range about 5 to 125 $\mu$m and the soap bar prepared from the coated powder having the thus defined particle size range impart the pearly luster and noble color quality to the soap bar which is interpreted as being that the soap base composition and the coated powder are not complexed each other, but simply mixed and dispersed thereby representing the natural color quality inherent in the coated powder itself.

The soap bar according to the present invention is prepared by mixing the soap base composition comprising amino acid derivatives and the coated micaceous powder, dissolving and molding the mixture. Each process step can conveniently be carried out according to the conventional process known to the skilled in the art. Briefly, the soap bar according to the present invention can be prepared by mixing amino acid derivatives with a prescribed amount of saccharide such as sugar, di-glycerine, 1,3-butylene glycol, and polyols, and a minor amount of a soap powder and surfactants and then dissolving the mixture into water-lower alcohols under heating to give a soap bar base composition having a melting point of below 100° C. The resulting soap base composition is then mixed with a pre-formed coated micaceous powder. After the base-powder mixture is dispersed homogeneously, the dispersant is molded after pouring it into a mold chase, cooled and hardened to prepare the soap bar. The soap bar thus prepared has a weak acidity of about pH 5.0~7.0 in 1% solution. Alternatively, the soap bar can desirably be prepared according to the process disclosed in Korean Patent Application No. 1996-033520 developed by the present inventor, the full disclosure of which is incorporated herein by a reference.

DESCRIPTION OF THE PREFERRED EMBODIMENTS

The present invention will be illustrated in greater detail by way of the following examples. The examples are presented for illustrative purpose only and should not be construed as limiting the invention, which is properly delineated in the claims.

EXAMPLE 1

The compositions of the soap bar bases and the coated micaceous powders used in the preparation of the soap bars according to the invention are set forth in Tables 1 and 2 below.

TABLE 1

| | Composition of soap bar base | | | | | | |
|---|---|---|---|---|---|---|---|
| | Amount by weight (g) | | | | | | |
| Component | sample A | B | C | D | E | F | G |
| TEA-cocoyl glutamate | 19.20 | 22.50 | 18.90 | 22.00 | 19.10 | 21.00 | 22.00 |
| TEA-lauroyl glutamate | 25.20 | 25.50 | 20.50 | 25.80 | 17.50 | 17.20 | 18.50 |
| TEA-stearoyl glutamate | 29.70 | 30.30 | 29.10 | 26.60 | 26.60 | 30.50 | 28.00 |
| ethanol | 4.30 | 2.50 | 3.40 | 3.80 | 2.80 | 2.00 | 4.50 |
| 1,3-butylene glycol | 3.00 | 1.60 | 2.00 | 2.50 | 3.40 | 3.50 | 1.50 |
| sodium plamitate | 1.20 | 3.50 | 1.50 | 2.50 | 3.00 | 1.75 | 2.25 |
| sodium laurate | 2.60 | 1.00 | 1.50 | 2.00 | 1.20 | 1.75 | 2.30 |
| diglycerine | 1.50 | 3.00 | 2.50 | 3.50 | 2.00 | 2.50 | 3.00 |
| sorbitol | 1.80 | 2.00 | 2.50 | 1.50 | 1.00 | 3.40 | 2.50 |
| cocoyl glycoside | 1.00 | 1.50 | 2.50 | 2.00 | 0.50 | 0.75 | 0.75 |
| sodium hydroxide | 2.08 | 2.60 | 0.98 | 1.95 | 0.32 | 0.12 | 2.80 |
| ethylenediaminetetra acetic acid disodium | 0.05 | 0.15 | 0.10 | 0.12 | 0.08 | 0.10 | 0.10 |
| tocopheryl acetate | 0.10 | 0.15 | 0.08 | 0.10 | 0.10 | 0.05 | 0.10 |
| urea | 0.12 | 0.10 | 0.15 | 0.08 | 0.05 | 0.10 | 0.10 |
| fragrance | trace amount | | | | | | |
| purified water | up to 100 g | | | | | | |

TABLE 2

| Composition of coated micaceous powder (based on the weight) | | | | | | | | | |
|---|---|---|---|---|---|---|---|---|---|
| | Content based on the kind of coated powder (%) | | | | | | | | |
| Component | sample a | b | c | d | e | f | g | h | i |
| mica | 56 | 58.3 | 64 | 47 | 45 | 52 | 27 | 39 | 76 |
| titanium dioxide | 44 | 37.8 | 14 | 3 | 47 | 45 | 58 | — | — |
| tin oxide | — | 3.9 | — | — | — | — | — | — | — |
| black iron oxide | — | — | 30 | — | — | — | — | 61 | — |
| red iron oxide | — | — | — | 50 | — | — | — | — | 24 |
| iron blue | — | — | — | — | 8 | — | — | | — |
| carmine | — | — | — | — | — | 3 | — | — | — |
| chromimum oxide green | — | — | — | — | — | — | 15 | — | — |
| particle size (μm) | below 15 | below 25 | below 60 | below 60 | below 60 | below 60 | below 60 | below 60 | below 125 |

The components as set forth in the Table 1 above were mixed to prepare soap base compositions having a melting point of below 100° C. Then, each of the base composition was mixed with 0.01 g of the coated micaceous powder shown in Table 2, dispersed homogeneously and finally molded according to the conventional process to prepare soap bars.

EXAMPLES 2 to 9

Soap bars were prepared in the same manner as in Example 1 except for modifying the amount of the coated powder as in Table 3.

TABLE 3

| Amount of coated powder | | | | | | | | |
|---|---|---|---|---|---|---|---|---|
| | Ex. 2 | Ex. 3 | Ex. 4 | Ex. 5 | Ex. 6 | Ex. 7 | Ex. 8 | Ex. 9 |
| Amount of powder (g) | 0.02 | 0.05 | 0.1 | 0.5 | 1 | 2.5 | 5 | 11.11 |

It was confirmed that the soap bars Aa through Gi prepared according to Examples 1 to 9, albeit slight, have a unique pearly appearance, a noble color quality and a high luster.

Experiment 1

The soap bar prepared according to the combination of Aa of Tables 1 and 2 was evaluated for the changes in the bubbling power and the hardness according to the addition of the coated micaceous powder. For comparison, the MILD CLEAN UP SOAP which is commercially available from the Siseido, Co., Ltd., Japan was used.

The bubbling power was measured by Ross & Miles equipment under the condition of 200 ml (1.0% solution in water) of sample amount at a temperature of 50° C. and the hardness of the sample soap having a dimension of 20×20×40 mm was measured with Rheo Meter under the condition of adaptor: No. 3, speed: 6 cm/min, measuring position: 1 cm, measuring temperature of 3° C. The results are set forth in Table 4 below.

TABLE 4

| Bubbling power and hardness test data | | |
|---|---|---|
| Powder content (% by weight) | Bubbling power (unit: mm) | Hardness |
| 0.00 | 265 | 120 |
| 0.01 | 268 | 122 |
| 0.25 | 273 | 126 |
| 0.50 | 280 | 134 |
| 1.00 | 274 | 140 |
| 2.50 | 270 | 132 |
| 5.00 | 268 | 125 |
| 8.00 | 266 | 123 |
| Comparative soap | 265 | 120 |

As can bee seen from the above results, the soap bars according to the present invention were generally excellent in the soap quality compared to the conventional one although there were minor differences in the values according to the amount of the coated micaceous powder.

As described in the above, the soap bar of the invention prepared by mixing the soap bar base composition comprising amino acid derivatives with the coated micaceous powder, dissolving and molding provides a pearlescent appearance with a noble color quality and a high luster. Therefore, it is possible to improve the soap quality and increase the bubbling power and hardness by a combination of the specific soap base composition and the coated powder of the invention.

What is claimed is:

1. A soap bar having a soap base composition containing amino acid derivatives having a melting point of below 100° C. and a coated micaceous powder wherein the soap base composition comprises 18.90~22.50% of TEA-cocoyl glutamate, 17.20~25.80% of TEA-lauryl glutamate, 26.60~30.50% of TEA-stearoyl glutamate, 2.00~4.50% of ethanol, 1.50~3.50% of 1,3-butyleneglycol, 1.20~3.50% of sodium palpitate, 1.00~2.60% of sodium laureate, 1.50~3.50% of di-glycerine, 1.00~3.40% of sorbitol, 0.50~2.50% of $C_8$–$C_{14}$ alkyl polyglucoside, 0.12~2.80% of sodium hydroxide, 0.05~0.15% of ethylenediaminetetraacetic acid disodium, 0.05~0.15% of tocopherol acetate, 0.05~0.15% of urea based on weight.

2. The soap bar according to claim 1, wherein the particle size of the coated micaceous powder is in the range of 5~500μm.

3. The soap bar according to claim 1, wherein the soap bar has a pH in the range of 5.0~7.0 in 1% solution.

4. A soap bar prepared from a soap base composition containing amino acid derivatives having a melting point of below 100° C., ethanol, 1,3-butyleneglycol, sodium palpitate, sodium laureate, di-glycerine, sorbitol, $C_8$–$C_{14}$ alkylpolyglycoside, sodium hydroxide, ethylenediaminetetraacetic acid disodium, tocopheryl acetate and urea, and a coated micaceous powder in which mica is coated with one or two more components selected from the group consisting of titanium dioxide, tin oxide, iron oxides, iron blue, carmine and chromium oxides wherein the amino acid derivatives comprises TEA-cocoylglutamate, TEA-lauroylglutamate and TEA-stearoyl glutamate and wherein the amount of soap base composition is in the range of 90~99.99% by weight and the amount of coated powder is in the range of 0.01~10.0% based on the weight of the soap bar raw material.

5. A soap bar prepared form a soap base composition according to claim 4 wherein the soap base composition comprises 18.90~22.50% of TEA-cocoyl glutamate, 17.20~25.80% of TEA-lauryl glutamate, 26.60~30.50% of TEA-stearoyl glutamate, 2.00~4.50% of ethanol, 1.50~3.50% of 1,3-butyleneglycol, 1.20~3.50% of sodium palpitate, 1.00~2.60% of sodium laureate, 1.50~3.50% of di-glycerine, 1.00~3.40% of sorbitol, 0.50~2.50% of $C_8$–$C_{14}$ alkyl polyglucoside, 0.12~2.80% of sodium hydroxide, 0.05~0.15% of ethylenediaminetetraacetic acid disodium, 0.05~0.15% of tocopherol acetate, 0.05~0.15% of urea based on weight containing amino acid derivatives having a melting point of below 100° C. and a coated micaceous powder.

6. The soap bar according to claim 4, wherein the particle size of the coated micaceous powder is in the range of 5~500$\mu$m.

7. The soap car according to claim 4, wherein the soap bar has a pH in the range of 5.0~7.0 in 1% solution.

* * * * *